Figure 1:
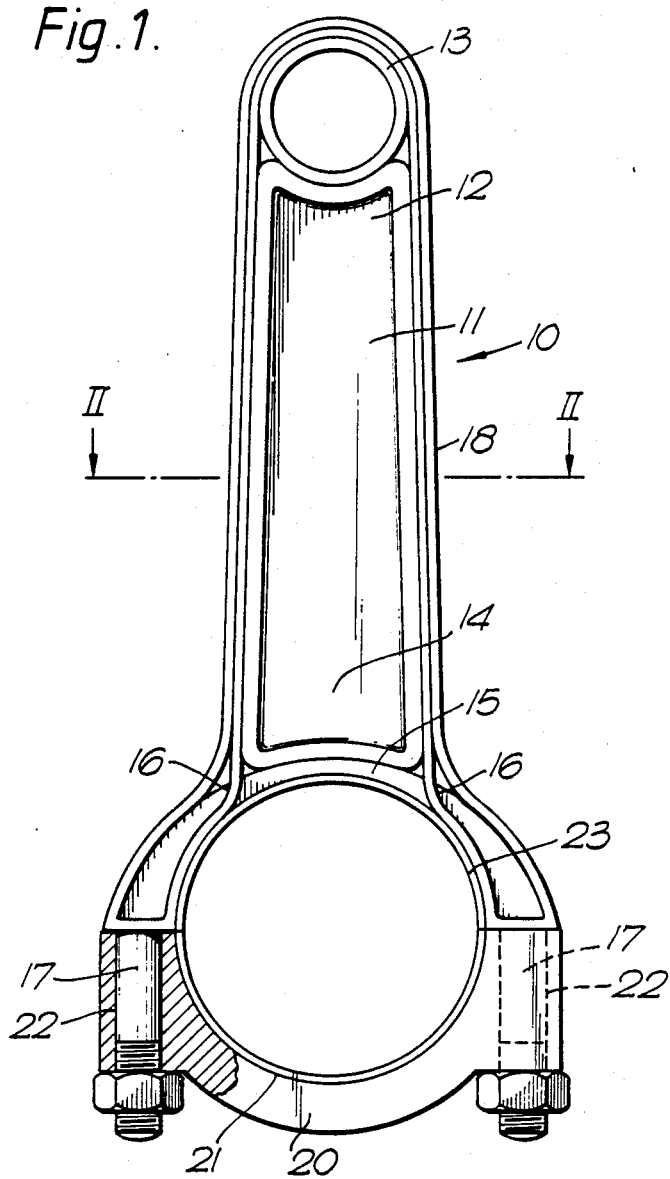

United States Patent [19]

Hughes et al.

[11] Patent Number: 4,905,540
[45] Date of Patent: Mar. 6, 1990

[54] FIBRE REINFORCED PLASTIC CONNECTING ROD

[75] Inventors: Joseph D. A. Hughes, Lanarkshire; Alan J. Wootton, Glasgow; Walter A. Lee, Strathaven; Alexander M. Mitchell, Glasgow, all of Scotland

[73] Assignee: The Secretary of State for Trade and Industry in her Britannic Majesty's Government of the United Kingdom of Great Britian and Northern Ireland, London, England

[21] Appl. No.: 929,110
[22] PCT Filed: Feb. 10, 1986
[86] PCT No.: PCT/GB86/00071
   § 371 Date: Oct. 17, 1986
   § 102(e) Date: Oct. 17, 1986
[87] PCT Pub. No.: WO86/04650
   PCT Pub. Date: Aug. 14, 1986

[30] Foreign Application Priority Data
   Feb. 12, 1985 [GB] United Kingdom ............... 8503535

[51] Int. Cl.$^4$ .............................................. G05G 1/00
[52] U.S. Cl. ............................... 74/579 E; 74/579 R; 123/197 AB
[58] Field of Search .............. 74/579 E, 579 R, 581; 123/197 AB; 29/156.5 A

[56] References Cited

U.S. PATENT DOCUMENTS

| | | | |
|---|---|---|---|
| 2,048,187 | 7/1936 | Hughes | 74/579 E |
| 2,738,687 | 3/1956 | Meile | 74/579 E |
| 3,815,431 | 6/1974 | Alvarez | 74/579 E |
| 4,184,384 | 1/1980 | Levine | 74/579 E |

FOREIGN PATENT DOCUMENTS

| | | | |
|---|---|---|---|
| 0033765 | 8/1981 | European Pat. Off. | 74/579 E |
| 897636 | 10/1953 | Fed. Rep. of Germany | 74/579 E |
| 3207573 | 9/1983 | Fed. Rep. of Germany | 74/579 E |
| 3329001 | 12/1984 | Fed. Rep. of Germany | 74/579 E |
| 7980 | of 1894 | United Kingdom | 74/579 E |
| 446728 | 5/1936 | United Kingdom | 74/579 E |
| 981446 | 1/1965 | United Kingdom | 74/579 E |
| 1364317 | 8/1974 | United Kingdom | 74/579 E |

OTHER PUBLICATIONS

Patents Abstracts of Japan, vol. 7, No. 279 (M-262) (1424) 13 Dec. 1983 and JP, A, 58156714 (Shigehiko) 9/17/83.
Patents Abstracts of Japan; vol. 9, No. 128 (M-384)(1851), 6/4/85 and JP, A, 60011713 (Mitsuya) 1/22/85.

Primary Examiner—Vinh T. Luong
Attorney, Agent, or Firm—Nixon & Vanderhye

[57] ABSTRACT

A connecting rod has a rod member formed from fiber reinforced plastic material secured to a cap member to define the big end of the connecting rod. Securement is by a metal member rigidly attached to the rod member, to which the cap member is secured. Attachment of the rod member and the metal member is via a locally transversely expanded end portion of the rod member enclosed within a similarly shaped (e.g. wedge shaped) cavity in the metal member such that the expanded end portion cannot be withdrawn axially of the rod member from the cavity.

12 Claims, 3 Drawing Sheets

FIBRE REINFORCED PLASTIC CONNECTING ROD

The present invention relates to fibre reinforced plastic connecting rods for machinery in which reciprocating motion is converted to rotary motion or vice versa.

There are many industrial uses of machines in which reciprocating motion is converted into rotary motion, the best known example being the internal combustion engine. In this type of machine a significant proportion of the energy lost results from the need to overcome the inertia of connecting rods. Connecting rods are used to transfer the reciprocating motion of pistons to rotary motion of a crankshaft. Connecting rods themselves have a motion which is a combination of linear and rotary.

Conventionally connecting rods have been made of metal, and in order to cut down the energy loss considerable effort has been devoted into reducing their weight. Efforts to reduce weight are, of course, complicated by the fact that connecting rods not only have to carry large forces to fulfil their function but have to sustain the effects of inertia forces due to their own weight. Recent advances in the technology of Fibre Reinforced Plastics (FRP) materials have made these materials suitable for use in the manufacture of connecting rods.

Connecting rods conventionally consist of a rod member having at one end, usually referred to as the little end, means for attaching the rod to a piston, and at the other end, commonly referred to as the big end, means for attaching the connecting rod to a crankshaft. To enable the rod to be connected to a crankshaft it is usually formed in two parts, having a cap member attachable to the rod member, the end of the rod and cap each including semi-circular portions which form a complete circle when the two are joined together.

The usual method of joining the rod and cap involves the use of nuts on bolts which pass through bores in the rod end and in the cap. This method is not ideal for connecting rods of FRP material. Drilling of bore holes in FRP material results in undesireable fracture of fibres. Manufacturing techniques for fabricating ends with bores therein in which fibres are not fractured are complicated and expensive. Also in FRP connecting rods with this type of end cap joint the cross-sectional area of the rod in the region of the bores has to be increased in order to withstand operational stresses. The increase can be such as to make such FRP connecting rods unsuitable for use in existing engine designs.

According to the present invention a connecting rod having a little end and a big end includes a Fibre Reinforced Plastic rod member, a cap member, and securing means for securing the rod and cap members together to define the big end, characterised in that the securing means includes a metal member, rigidly attached to the rod member, to which the cap member can be secured.

In one form of the invention the metal member is in the form of a saddle which is integrally united with the rod member by, for example, winding FRP material round appropriately designed saddle structure and round the rod member.

In another form of the invention the metal member and rod are so adapted that the metal member encloses a locally expanded end of the rod member. In this form of the invention the end of a rod member of rectangular section might be locally expanded on two opposite sides in wedge-like fashion and dove-tailed into a wedge-shaped channel in the metal member. Alternatively the end of the rod might be caused to fit into a frusto-pyramidal or frusto-conical cut-out in the metal member by, for example, injection moulding of thermoplastic material under appropriate conditions of temperature and pressure.

The cap member may be formed from metal, from FRP material, or from a combination of metal and FRP material.

Figure 2:
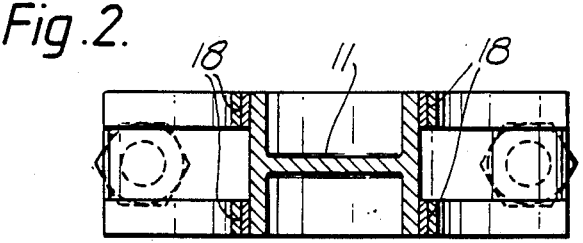
Figure 3:
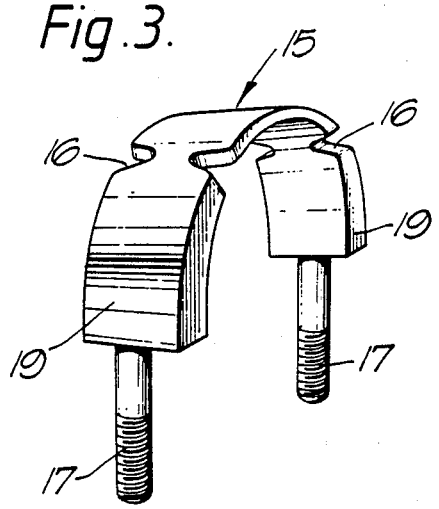
Figure 4:
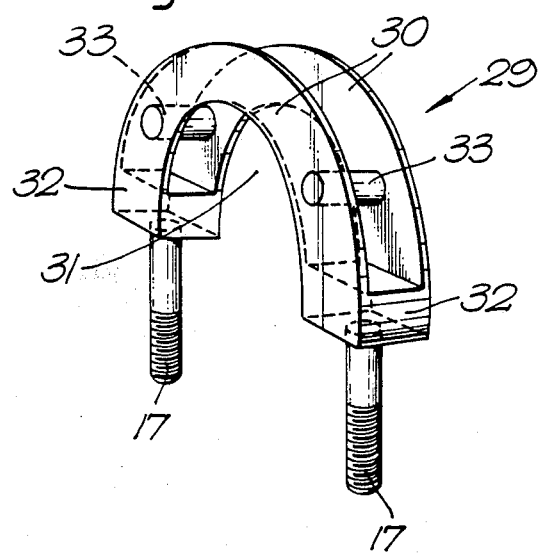
Figure 5:
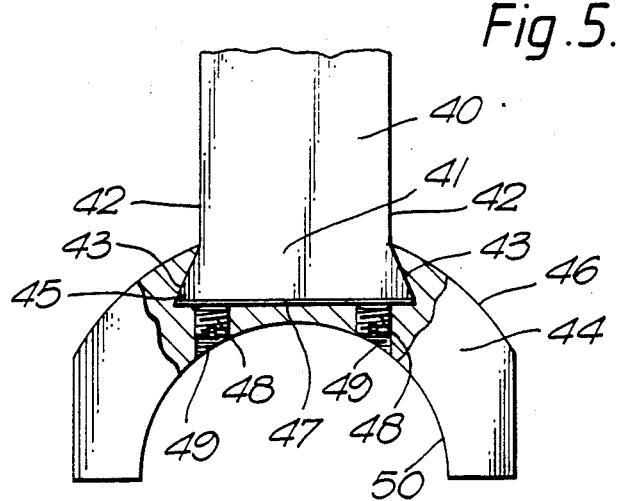
Figure 6:
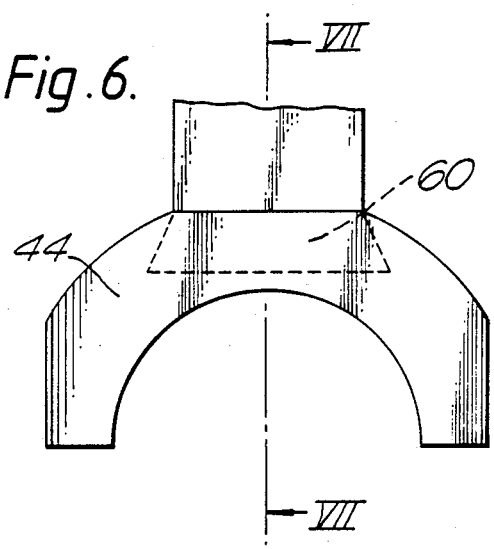
Figure 7:
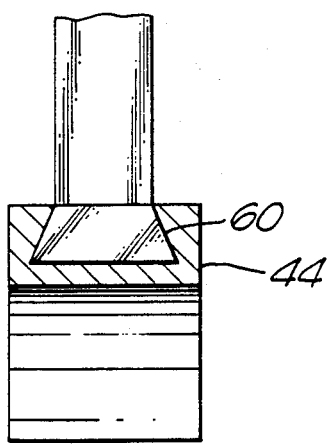

Some embodiments of the invention will now be described, by way of example only, with reference to the accompanying diagrammatic drawings, of which:

FIG. 1 is an elevation, partly in section, of a connecting rod according to the invention and including a metal saddle, FIG. 2 is a plan view, in section along line II—II of FIG. 1, of the connecting rod, FIG. 3 is a perspective view of a saddle as used in the connecting rod illustrated in FIGS. 1 and 2, FIG. 4 is a perspective view of another form of saddle suitable for use in the invention, FIG. 5 is an elevation, partly in section, of another embodiment of the invention, FIG. 6 is an elevation of a modified form of the embodiment of FIG. 5, and FIG. 7 is an elevation in section along line VII—VII of FIG. 6.

A connecting rod has a rod member 10 having a central compression member 11 formed of FRP and of I-Section (see FIG. 2). A first end 12 of the central compression member 11 bears against a tubular insert 13 and a second end 14 bears against a metal saddle 15. The metal saddle 15 is of semi-circular shape and has adjacent each end a pair of slots 16 extending part way across the width thereof. Mutually parallel clamping bolts 17 extend from the ends of the saddle 15. Continuous FRP overwraps 18 extend round the tubular insert 13, central compression member 11, round arms 19 between ends of the metal saddle 15 and the slots 16 and through the slots 16.

An end cap 20, which may be of metal or of FRP material has an internal semi-circular channel 21 of substantially identical diameter to the diameter of the metal saddle 15. Parallel holes 22 extend through the end cap 20.

In use the tubular insert 13 is attached to a piston (not shown) by means, for example, of a gudgeon pin. The semi-circular metal saddle 15 is positioned over a bearing shell 23 on a journal portion of a crankshaft (not shown) and the end cap 20 is positioned so that it also overlies the bearing shell 23 with the bolt members 17 passing through the holes 22. Nuts 24 are tightened on the studs 17 to hold the rod member 10 and cap member 20 rigidly together.

In an alternative form of saddle 29 (FIG. 4) two semi-circular metal plates 30 each having a semi-circular channel 31 therein are connected at their ends by metal blocks 32 to which are secured mutually parallel clamping bolts 17. Metal bars 33 extend between plates 30 and the saddle is secured to a rod member (such as rod member 10 of FIGS. 1 and 2, not shown here) by wrapping FRP material round the bars 33 in a manner similar to that in which overwraps 18 pass round arms 19 in the embodiment of the invention as described above with reference to FIGS. 1 to 3. The space between the plates 30 not occupied by metal blocks 32 and metal bars 33 may be filled with FRP material, which may be integral with FRP material of a rod member such as the rod member 10 described above.

An end cap, such as an end cap 20, may be attached to a rod member including a saddle 29 in the same way as to a rod member 10.

Another embodiment of the invention (FIG. 5) has a FRP material rod member 40 of substantially rectangular form. An end 41 remote from the little end (not shown) of the rod member constitutes an expanded end portion in that it has two opposite faces 42 expanded to form wedge shaped projections 43. A metal member 44 of substantially semi-annular form has a cavity in the form of a wedge shaped channel 45 extending therethrough normal to the plane of the member 44 and extending inwardly from a mouth at the midpoint of an outer surface 46 thereof.

The end 41 of the rod 40 is introduced into the channel 45 to form a dove tail joint. By virtue of the wedge shapes, the channel mouth defined between edges 45a is of smaller transverse dimension than a corresponding transverse dimension of the expanded end portion of the rod within the channel 45 such that the expanded end portion cannot be withdrawn axially of the rod member from the cavity. With this embodiment of the invention it may sometimes be advantageous, in order to ensure a tight fit between the wedge shaped projections 43 and sides of the channel 45, to fit a shim 47 between a base of the channel 45 and the end 41 of the rod 40. Complete rigidity can be ensured by the use of grub screws such as those shown at 48 which are screwed into tapped holes 49 which enter inwardly from an inner surface of member 44. The screws 48 are preferably of a length such that when tight they stand proud of the surface 50. They are then machined flush with the surface 50. When the connecting rod is assembled the screws 48 are locked in position by the presence of bearing shell 23.

In an alternative form of the last above described embodiment (FIGS. 6 and 7) the member 44 has a frusto-pyramidal cut-out 60 therein. An end 41 of a rod member 40 is expanded into the cut-out 60 to be secured therein. Expansion of the end 41 can be accomplished by, for example, injection moulding a short-fibre reinforced thermoplastic material around the end 41 and into the cut-out 60. The end 41 might have means, such as an annular channel (not shown) to which the thermoplastic material becomes keyed.

The cut out 60 can be formed by machining, or the member 44 can be formed in two annularly divided parts, with slots therein. The two parts can then be joined, such that the slots combine to give the cut-out 60 by, for example, welding or bolting.

When the member 44 is formed in two parts they may be assembled together round an end 41 of a rod 40 which has been pre-formed to the shape of the cut-out 60. In this case it might be necessary, for complete rigidity, to use shims such as 47, grub screws such as 48 and tapped holes such as 49 similar to those in the embodiment described above with reference to FIG. 5.

It might also be possible, depending on the nature of the FRP material used for rod member 40, to cast metal members 44 round a pre-formed end 41 of the rod member 40.

The rigidly attached rod member 40 and metal member 44 can be connected to a cap member such as 20 by means well known in the art. For example mutually parallel studs (not shown) may be made integral with the ends of the member 44. Alternatively holes (not shown) may be tapped in the ends of the member 44 to allow bolts to be screwed therein after passage through holes in the cap member 20.

Those skilled in the art will realise that many embodiments of the invention are possible; for example whilst the studs 17 are described and illustrated as being integral with the metal saddles 15, 29 they may in practice be replaced by bolts extending through holes in the metal saddles 15, 19. Alternatively, of course, bolts passing through bores in the end cap 20 may be screwed into tapped holes in the metal members 15, 19. Likewise FRP materials suitable for use with the invention will be well known to those skilled in the art and hence will not be described in detail herein.

Various constructions of rod members 10, 40 will be readily apparent to those skilled in the art.

When a rod member 40 of circular cross-section can advantageously be used it may be secured to a metal member 44 by means similar to those of the embodiments described above with reference to FIGS. 6 and 7 but using a frusto-conical cut-out 60. Other shapes of cut-out suitable for use with the invention—for example cut-outs having curved faces—will be readily apparent.

What is claimed is:

1. A connecting rod, having a little end and a big end, including a Fibre Reinforced Plastic rod member, a cap member, and means for securing the rod and cap members together to define the big end, characterised in that the securing means includes a metal member, rigidly attached to the rod member, to which the cap member can be secured, the rod member having a locally transversely expanded end portion enclosed within a similarly shaped cavity in the metal member such that the expanded end portion cannot be withdrawn axially of the rod member from the cavity, the cavity having a mouth through which the rod extends, the mouth of the cavity being of smaller transverse dimension than a correspondingly transverse dimension of the expanded end portion within the cavity.

2. A connecting rod as claimed in claim 1 characterised in that the end of the rod member is of rectangular cross section and has two opposite sides expanded to form wedge shaped projections having transversely outer sides which bear against corresponding sides of a correspondingly wedge shaped channel in the metal member.

3. A connecting rod as claimed in claim 2 characterised in having means for forcing the transversely outer sides of the wedge shaped projections into pressurised contact with the corresponding sides of the correspondingly wedge shaped channel.

4. A connecting rod as claimed in claim 3 characterised in that the wedge shaped channel has a channel bottom, and the means for forcing the transversely outer sides of the wedge shaped projections into contact with the corresponding sides of the channel include a shim between the rod end and the channel bottom and screws in bores in the metal member and bearing against said shim.

5. A connecting rod as claimed in claim 1 characterised in that the end of the rod member is expanded to fill a cut-out in the metal member.

6. A connecting rod as claimed in claim 5 characterised in that the expanded end of the rod and the cut-out are of frusto-pyramidal form.

7. A connecting rod as claimed in claim 5 characterised in that the end of the rod member is secured in the cut out by the expansion thereof by injection moulding thereon of material.

8. A connecting rod as claimed in claim 7 wherein the end of the rod member is adapted such that the injection moulded material becomes keyed thereon.

9. A connecting rod as claimed in claim 5 characterised in having means for forcing the transverse sides of the expanded end of the rod member into pressurised contact with sides of the cut-out.

10. A connecting rod as claimed in claim 9 characterised in that the cut-out has a bottom, and the means for forcing the transverse sides of the expanded end of the rod member into pressurised contact with sides of the cut-out include a shim between the rod end and the cut-out bottom and screws in bores of the metal member and bearing against the shim.

11. A connecting rod as claimed in claim 1 characterised in that means for securing the rod member to the cap member also includes studs which are secured to the metal member and which pass through holes in the cap member.

12. A connecting rod as claimed in claim 1 wherein the locally transversely expanded end portion comprises wedge shaped surface portions tapering transversely outwardly as they approach said big end from said little end, and said cavity has correspondingly formed and dimensioned interior surface portions.

* * * * *